(12) United States Patent
Koh

(10) Patent No.: US 7,179,229 B1
(45) Date of Patent: Feb. 20, 2007

(54) SYSTEM AND METHOD FOR APNEA DETECTION USING BLOOD PRESSURE DETECTED VIA AN IMPLANTABLE MEDICAL SYSTEM

(75) Inventor: Steve Koh, Rowland Heights, CA (US)

(73) Assignee: Pacesetter, Inc., Sylmar, CA (US)

( * ) Notice: Subject to any disclaimer, the term of this patent is extended or adjusted under 35 U.S.C. 154(b) by 364 days.

(21) Appl. No.: 10/821,241

(22) Filed: Apr. 7, 2004

(51) Int. Cl.
  *A61B 5/00* (2006.01)
(52) U.S. Cl. .................. 600/485; 600/483; 600/500
(58) Field of Classification Search ............... 600/484, 600/500, 485, 503
See application file for complete search history.

(56) References Cited

U.S. PATENT DOCUMENTS

| | | | |
|---|---|---|---|
| 3,957,036 A | 5/1976 | Normann | 128/2.1 R |
| 5,056,519 A | 10/1991 | Vince | 128/419 G |
| 5,476,483 A | 12/1995 | Bornzin et al. | 607/17 |
| 5,817,135 A | 10/1998 | Cooper et al. | 607/17 |
| 5,911,218 A | 6/1999 | DiMarco | 128/200.24 |
| 6,314,323 B1 | 11/2001 | Ekwall | 607/23 |
| 6,331,536 B1 | 12/2001 | Radulovacki et al. | 514/214.02 |
| 6,415,183 B1 | 7/2002 | Scheiner et al. | 607/42 |
| 6,432,956 B1 | 8/2002 | Dement et al. | 514/252.1 |
| 6,466,821 B1 | 10/2002 | Pianca et al. | 607/18 |
| 6,519,493 B1 | 2/2003 | Florio et al. | 607/9 |
| 6,520,917 B1* | 2/2003 | Kunig et al. | 600/481 |
| 6,525,073 B2 | 2/2003 | Mendel et al. | 514/337 |
| 6,586,478 B2 | 7/2003 | Ackman et al. | 514/738 |
| 6,616,613 B1 | 9/2003 | Goodman | 600/504 |
| 6,641,542 B2* | 11/2003 | Cho et al. | 600/529 |
| 6,658,292 B2 | 12/2003 | Kroll et al. | 607/19 |
| 6,881,192 B1* | 4/2005 | Park | 600/529 |
| 2003/0036685 A1 | 2/2003 | Goodman | 600/300 |
| 2003/0130703 A1 | 7/2003 | Florio et al. | 607/11 |
| 2003/0153954 A1 | 8/2003 | Park et al. | 607/17 |
| 2005/0115561 A1* | 6/2005 | Stahmann et al. | 128/200.24 |

* cited by examiner

*Primary Examiner*—Charles A Marmor, II
*Assistant Examiner*—Karen E Toth

(57) ABSTRACT

Techniques are provided for detecting non-obstructive forms of apnea within a patient using an implantable medical system based on changes in blood pressure. The implantable system monitors for any substantially uniform decease in diastolic blood pressure over a series of heartbeats. If the uniform decease is sustained from beat to beat over a sufficient period of time, typically only ten seconds, non-obstructive apnea is deemed to have commenced and appropriate therapy may then be delivered. Preferably, however, therapy is only delivered if the episode of apnea is corroborated based on thoracic impedance signals, accelerometer signals or the like. In this manner, an episode of non-obstructive apnea can be promptly and reliably detected, thus allowing for prompt delivery of therapy.

31 Claims, 7 Drawing Sheets

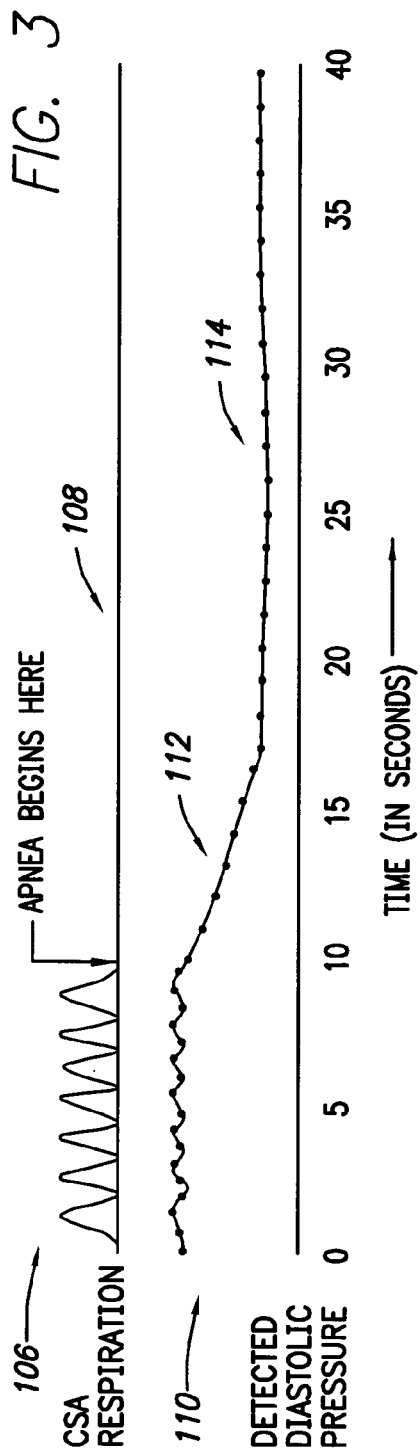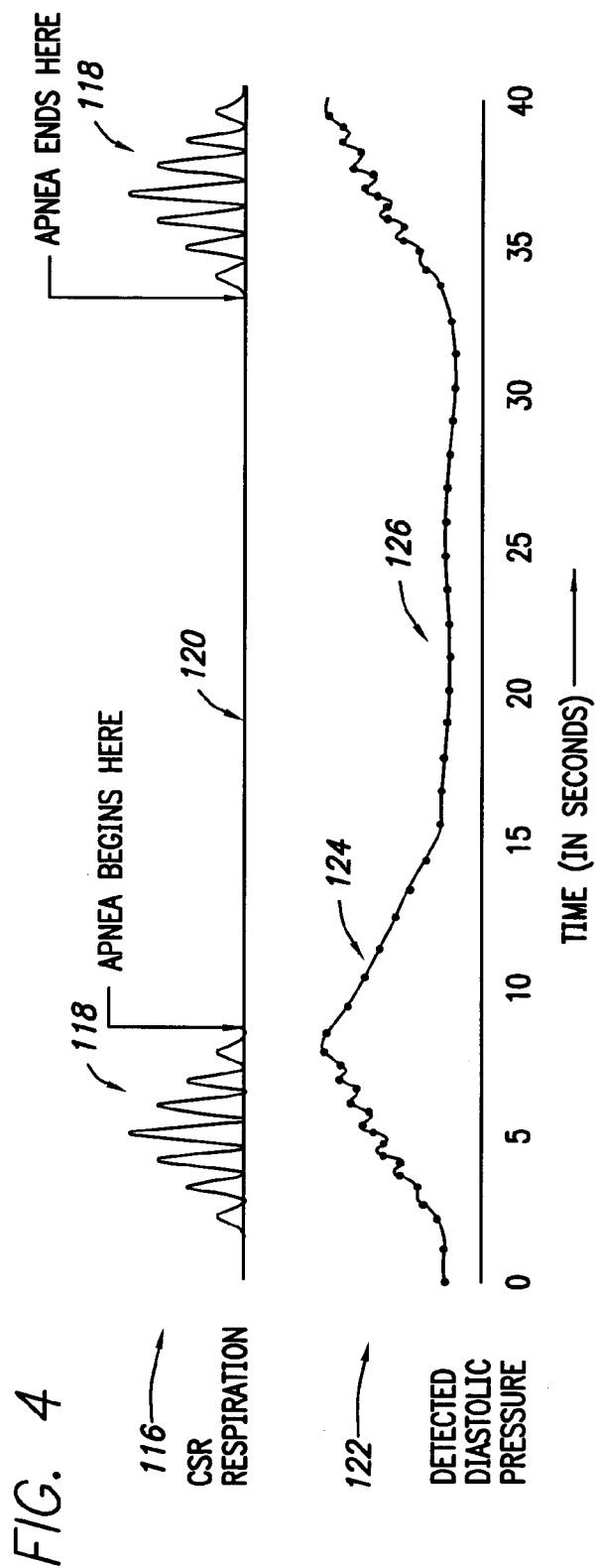

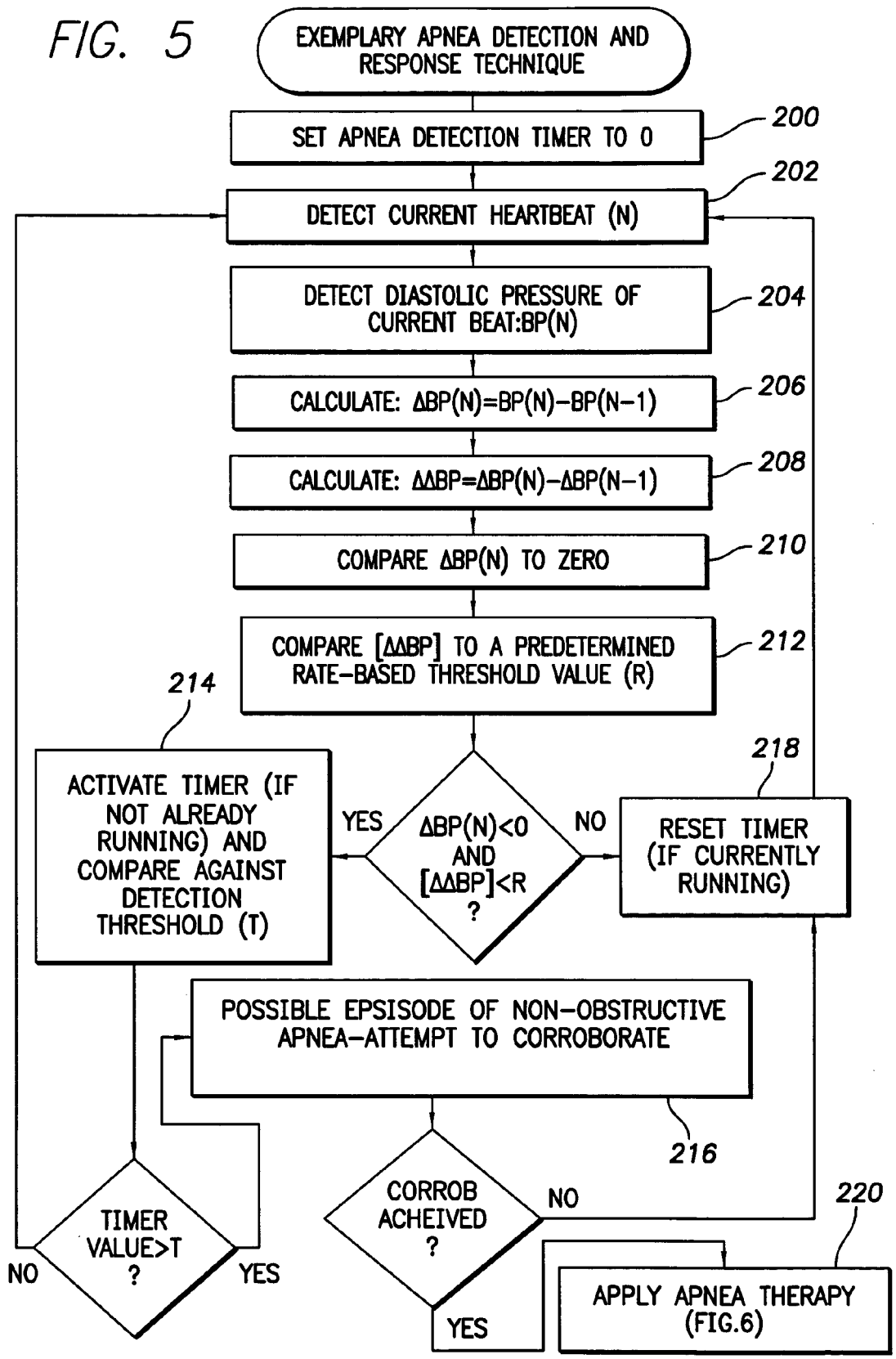

FIG. 8

SYSTEM AND METHOD FOR APNEA DETECTION USING BLOOD PRESSURE DETECTED VIA AN IMPLANTABLE MEDICAL SYSTEM

FIELD OF THE INVENTION

The invention generally relates to implantable medical devices, such as pacemakers or implantable cardioverter/defibrillators (ICDs), and in particular to techniques for detecting apnea within a patient in which a medical device is implanted and for delivering therapy in response thereto.

BACKGROUND

Apnea is a disorder characterized by temporary, recurrent interruptions of respiration. With apnea, respiration may cease completely for a minute or longer. One common form of apnea is sleep apnea, in which individual episodes of apnea can occur hundreds of times during a single night. Accordingly, patients with sleep apnea experience periodic wakefulness at night and excessive sleepiness during the day. In addition, apnea can exacerbate various medical conditions, particularly congestive heart failure (CHF) wherein the patient suffers from poor cardiac function. Other medical conditions that can be adversely affected by sleep apnea include: high blood pressure, risk for heart attack and stroke, memory problems, impotency and sexual dysfunction, migraine headaches, depression and anxiety, polycythemia (increase in the number of red blood cells), cor pulmonale (enlarged left ventricle of the heart), bradycardia (excessively slow heart rate), tachycardia (excessively fast heart rate), pulmonary hypertension hypoxemia (chronic daytime low blood oxygen) and hypercapnia (increased blood carbon dioxide ($CO_2$)).

One form of sleep apnea is central sleep apnea (CSA), which is believed to be the result of a neurological condition. Briefly, respiration is regulated by groups of nerve cells in the brain in response to changing blood chemistry levels, particularly blood $CO_2$ levels. When blood $CO_2$ levels exceed a certain threshold, the groups of nerve cells generate a burst of nerve signals for triggering inspiration. The inspiration nerve signals are relayed via phrenic nerves to the diaphragm and via other nerves to chest wall muscles, which collectively contract to expand the lungs. With CSA, the nerve signals are not properly generated during extended periods of time while the patient is asleep or are of insufficient magnitude to trigger sufficient muscle contraction to achieve inhalation. In either case, the patient thereby fails to inhale until appropriate inspiration nerve signals are eventually generated—often not until after the patient awakes in response to significantly high blood $CO_2$ levels. Arousal from sleep due to CSA usually lasts only a few seconds, but such brief arousals nevertheless disrupt continuous sleep leading to excessive sleepiness during the day, which diminishes quality of life. Excessive sleepiness during the day also increases risks due to accidents, particularly automobile accidents caused by the driver falling asleep due to the excessive daytime sleepiness. In addition, as already noted, frequent periods of apnea can exacerbate other medical conditions. In particular, aberrant blood chemistry levels occurring by sleep apnea are a significant problem for patients with CHF. Due to poor cardiac function caused by CHF, patients already suffer from generally low blood oxygen levels. Frequent periods of sleep apnea result in even lower blood oxygen levels. Fortunately, CSA is rare.

Another form of sleep apnea, which is more common, is obstructive sleep apnea (OSA) wherein the respiratory airway is temporarily blocked. With OSA, proper inspiratory nerve signals are generated by the brain and so the diaphragm and chest muscles contract in an attempt to cause the lungs to inhale. However, an obstruction of the upper respiratory airway blocks delivery of air to the lungs and so blood $CO_2$ levels continue to increase, usually until the patient awakens and adjusts his or her position so as to reopen the obstructed respiratory airway so that normal breathing can resume. The site of obstruction is usually the soft palate, near the base of the tongue, which lacks rigid structures such as bone or cartilage for keeping the airway open. While the patient is awake, muscles near the soft palate keep the passage open. However, while asleep, the muscles can relax to a point where the airway collapses and hence becomes obstructed. As with CSA, arousal from sleep usually lasts only a few seconds but is sufficient to disrupt continuous sleep and prevent proper REM sleep.

Apnea can also occur during Cheyne-Stokes Respiration (CSR), which is an abnormal respiratory pattern often occurring in patients with CHF. CSR is characterized by alternating periods of hypopnea (i.e. reduced breathing) and hyperpnea (i.e. fast, deep breathing.) Briefly, CSR arises principally due to a time lag between blood $CO_2$ levels sensed by the respiratory control nerve centers of the brain and the blood $CO_2$ levels. With CHF, poor cardiac function results in poor blood flow to the brain such that the respiratory control nerve centers respond to blood $CO_2$ levels that are no longer properly representative of the overall blood $CO_2$ levels in the body. Hence, the respiratory control nerve centers trigger an increase in the depth and frequency of breathing in an attempt to compensate for perceived high blood $CO_2$ levels—although the blood $CO_2$ levels have already dropped. By the time the respiratory control nerve centers detect the drop in blood $CO_2$ levels and act to slow respiration, the blood $CO_2$ levels have already increased. This cycle becomes increasingly unbalanced until respiration alternates between hypopnea and hyperpnea. The periods of hypopnea often become sufficiently severe that no breathing occurs between the periods of hyperpnea, i.e. periods of frank apnea occur between the periods of hyperpnea. The wildly fluctuating blood chemistry levels caused by alternating between hyperpnea and apnea can exacerbate CHF and other medical conditions. Moreover, CSR can prevent the patient from achieving rapid eye movement (REM) sleep, which is needed. In this regard, REM sleep does not usually occur until after some period of the sustained Stage 3/Stage 4 sleep. CSR usually arises during Stage 3 sleep. Hence, repeated sleep interruptions occurring during CSR typically prevent the patient from achieving any REM sleep or, at least, an insufficient amount of REM sleep is achieved over the course of the night. When CHF is still mild, CSR usually occurs, if at all, only while the patient is sleeping. When it becomes more severe, CSR can occur while the patient is awake. Accordingly, CSR is one mechanism by which apnea can occur within patients who are awake.

In view of the significant adverse consequences of apnea, particularly insofar as patients with CHF are concerned, it is highly desirable to provide techniques for detecting and treating the condition. Apnea arising due to CSR is usually treated by addressing the source of the CSR, such as an underlying CHF. By reducing CHF so as to improve stroke volume, CSR is less likely to occur and so any periods of apnea arising during CSR may be avoided. OSA is usually treated by having the patient wear a breathing apparatus at night, such as a device providing continuous positive airway pressure (CPAP) therapy or bi-level positive pressure therapy (Bi-PAP). Surgery, however, is sometimes necessary. Although the source of CSA appears to be neurological, breathing devices employing CPAP or B-PAP techniques have been found to be effective for treating CSA as well. Although such breathing devices are effective when properly employed, they are often uncomfortable and inconvenient for the patient and, as a result, many patients fail to wear the device each night and hence forfeit the benefits thereof. In addition, when properly worn, the devices apply therapy continuously—even on nights when the patient might not have any actual episodes of sleep apnea.

Thus, many of these forms of therapy are delivered more or less continuously, at least while the patient is asleep, even when no episodes of apnea are occurring. In many cases, it would instead be desirable to automatically detect individual episodes of apnea and deliver therapy only as needed. In particular, it would desirable to provide such capability within an implantable medical system. Properly equipped, an implantable medical system could detect the onset of individual episodes of apnea and deliver appropriate therapy based upon the type of apnea. If an episode of non-obstructive apnea is detected, the device could then deliver periodic stimulation signals to the diaphragm via direct electrical stimulation of the phrenic nerves to cause the diaphragm to resume a proper respiratory rhythm. Within implantable systems lacking nerve stimulators for directly terminating the episode of apnea, warning signals may instead be generated (either via an implanted warning device or a bedside monitor) for awakening or otherwise alerting the patient so as to cause the patient to resume normal breathing. In any case, by promptly detecting the onset of an individual episode of apnea, therapy or warning signals can be promptly initiated so as to provide for prompt termination of the episode of apnea, thus reducing its adverse effects. Such as implantable medical system could utilize a pacemaker or ICD for use as a controller to coordinate the detection of episodes of apnea and the delivery of therapy in response thereto. Pacemakers and ICDs are usually implanted primarily for use in applying cardiac therapy for treating cardiac arrhythmias. However, many patients who are candidates for pacemakers or ICDs also suffer from apnea and hence could benefit from additional functionality directed to the detection and treatment of apnea.

Hence, it would be highly beneficial to provide techniques for detecting the onset of individual episodes of apnea, particularly for use within implantable medical systems. Heretofore, however, prompt and reliable detection of the onset of individual episodes of apnea has proven to be problematic. Even in the absence of apnea, respiration is often fairly infrequent (particularly while a patient is asleep) and so the lack of respiration for some period of time does not necessarily indicate the onset of apnea. False detection of apnea, when a patient is otherwise breathing properly, can result in unnecessary or improper therapy. Accordingly, to avoid such false positives, many conventional automatic apnea detection techniques require that no respiration be detected for some extended period of time—often twenty seconds or more—before an indication of apnea is made. By then, however, if apnea is indeed occurring, it has already been ongoing for some time and so prompt detection is not achieved.

Accordingly, it would be highly desirable to provide techniques for providing for faster detection of the onset of an individual episode of apnea and it is to this end that the invention is primarily directed. More specifically, the invention is primarily directed to detecting non-obstructive forms of apnea, such as CSA and apnea arising due to CSR.

SUMMARY

In accordance with a first embodiment, techniques are provided for detecting non-obstructive forms of apnea within a patient using an implantable medical system based on changes in blood pressure. In an exemplary embodiment, the implantable system operates to detect a substantially uniform decease in diastolic blood pressure over a series of heartbeats. If the substantially uniform decrease in pressure continues for at least ten seconds, non-obstructive apnea is deemed to have commenced.

In one example, the substantially uniform decrease in diastolic blood pressure down to a stable baseline blood pressure is detected using the following technique. $BP(n)$ is tracked over a plurality of heartbeats, wherein $BP(n)$ is the blood pressure of heartbeat "n". Then $\Delta BP(n)$, which represents the change in blood pressure from one beat to the next, is calculated based on $\Delta BP(n)=BP(n)-BP(n-1)$. Next, $\Delta\Delta BP$, which represents the change in the rate of change in blood pressure from one beat to the next, is calculated based on $\Delta\Delta BP=\Delta BP(n)-\Delta BP(n-1)$. If $\Delta BP(n)$ is found to be negative and $|\Delta\Delta BP|$ is found to be less than a predetermined rate-based threshold value (R), a timer is activated. So long as $\Delta BP(n)$ remains negative and $|\Delta\Delta BP|$ remains less than R, the timer continues to operate. The timer thereby tracks any time interval where the blood pressure is decreasing and the rate of change of blood pressure is substantially constant. If the timed period exceeds an apnea detection threshold, set to ten seconds, the onset of non-obstructive apnea is thereby detected. In some cases, the blood pressure will stabilize at a low baseline pressure before the timer expires. If so, then the timer remains active to additionally track the period of stable blood pressure. If the total time (i.e. the time in which the blood pressure decreases uniformly combined with the time in which the blood pressure remains stable) exceeds the apnea detection threshold, non-obstructive apnea is also detected. In either case, an episode of non-obstructive apnea is detected ten seconds following its onset, thus allowing prompt delivery of therapy. Preferably, however, therapy is only delivered if the episode of apnea is corroborated based on, for example, an evaluation of thoracic impedance signals.

If the implantable system is equipped with a phrenic nerve stimulator, therapy may be in the form of diaphragmatic pacing. However, other types of therapy may be employed, either additionally or in the alternative. For example, aggressive cardiac overdrive pacing may be delivered during the episode of apnea in an attempt to trigger respiration. Alternatively, an alarm device may be triggered to awaken the patient upon detection of an episode of apnea (assuming the patient is sleeping). The alarm device may be an implanted device or a bedside warning system. In either case, the patient is thereby awakened once an episode of apnea is detected to prevent extended episodes of apnea, which can eventually cause significant variances in blood chemistry that exacerbate other medical conditions such as CHF. In addition, once a determination has first been made by the implanted system that the patient is subject to non-obstructive apnea, drug therapy or mild overdrive pacing may be delivered in an effort to prevent additional episodes of apnea from occurring. In one specific example, warning alarms are generated to awaken the patient only if other forms of therapy are unsuccessful in preventing or terminating episodes of apnea. In addition, regardless of the type of therapy, diagnostic information representative of the episodes of apnea is preferably recorded within a memory of the implanted system for subsequent review by a physician.

Hence, techniques are provided for promptly detecting an episode of non-obstructive apnea and for delivering appropriate therapy.

BRIEF DESCRIPTION OF THE DRAWINGS

The above and further features, advantages and benefits will be apparent upon consideration of the present description taken in conjunction with the accompanying drawings, in which:

FIG. 3 is a graph illustrating exemplary respiration and blood pressure patterns analyzed via the technique of FIG. 2 and, in particular, illustrating a substantially uniform decrease in diastolic blood pressure occurring following the onset of an episode of CSA;

FIG. 4 is a graph illustrating additional exemplary respiration and blood pressure patterns analyzed via the technique of FIG. 2 and, in particular, illustrating a substantially uniform decrease in diastolic blood pressure occurring following the onset of an episode of apnea during CSR;

FIG. 5 is a flow diagram illustrating an exemplary technique performed by the system of FIG. 1 for detecting the onset of an episode of non-obstructive apnea and for delivering appropriate therapy;

FIG. 8 is a functional block diagram of the pacer/ICD of FIG. 7, illustrating basic circuit elements that provide cardioversion, defibrillation and/or pacing stimulation in four chambers of the heart and particularly illustrating internal components for performing the techniques of FIGS. 2–5 to detect non-obstructive apnea and to control deliver of therapy in response thereto.

DETAILED DESCRIPTION OF THE PREFERRED EMBODIMENTS

The following description includes the best mode presently contemplated for practicing the illustrative embodiments. The description is not to be taken in a limiting sense but is made merely to describe general principles of the illustrative embodiments. The scope of the invention should be ascertained with reference to the issued claims. In the description that follows, like numerals or reference designators will be used to refer to like parts or elements throughout.

Overview of Implantable Apnea Responsive System

Figure 1:
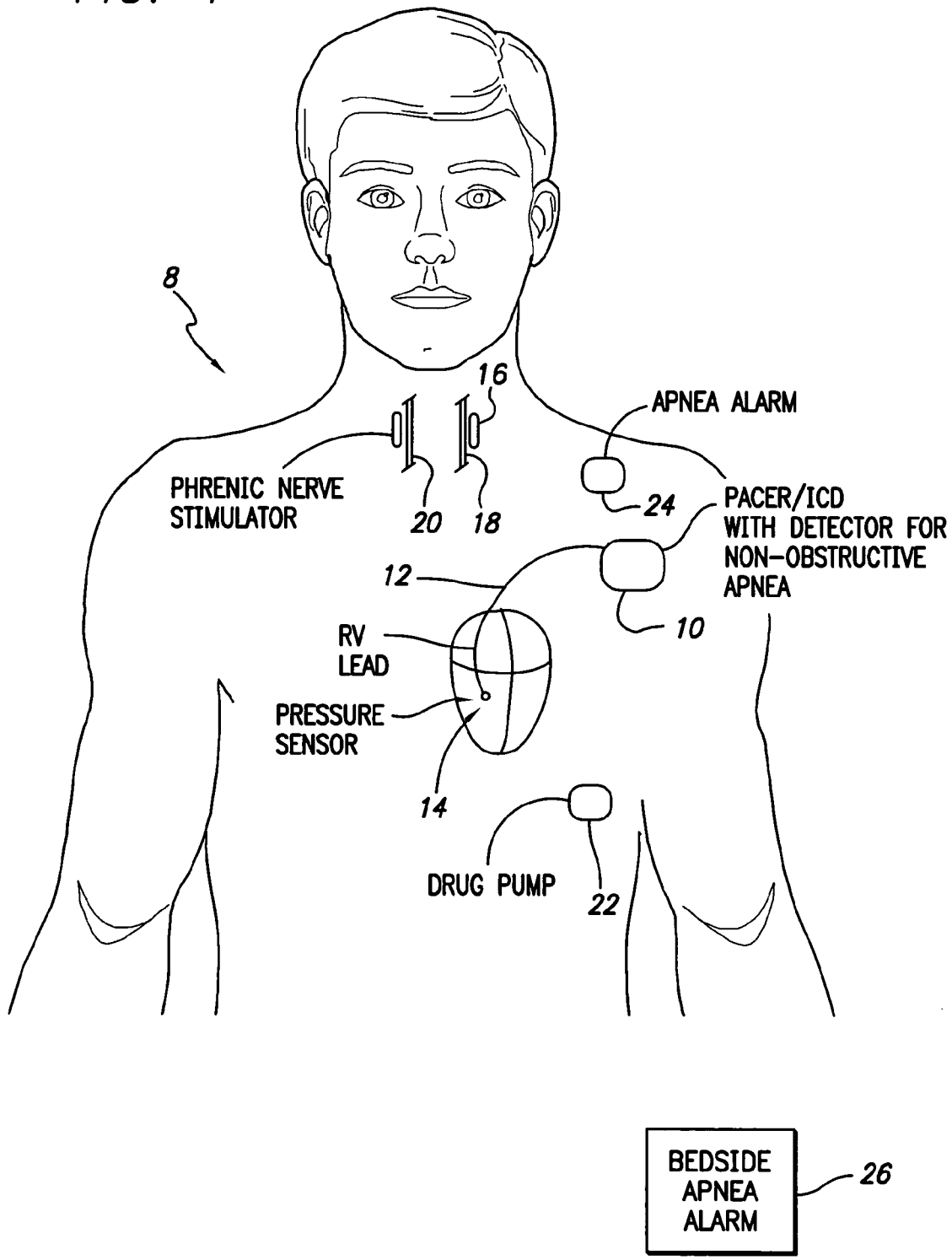
FIG. 1 illustrates pertinent components of an implantable apnea responsive medical system having a pacer/ICD capable of detecting non-obstructive forms of apnea based on changes in blood pressure and having additional components for delivering therapy or warning signals in response thereto.

FIG. 1 illustrates an implantable apnea responsive medical system 8 capable of detecting individual episodes of non-obstructive forms of apnea, such as CSA or apnea arising due to CSR, based primarily on changes in blood pressure. To this end, pacer/ICD 10 receives signals representative of blood pressure from a right ventricular (RV) lead 12 equipped with a pressure sensor 14 and determines therefrom the diastolic pressure of the patient. The pressure sensor may be, for example, a piezoelectric device mounted at or near the tip of the lead. A suitable pressure sensor for use in the ventricles is described in U.S. Pat. No. 6,314,323 to Ekwall, entitled "Heart Stimulator Determining Cardiac Output, By Measuring The Systolic Pressure, For Controlling The Stimulation," which is incorporated by reference herein. Briefly, non-obstructive apnea is detected by identifying periods of time exhibiting a substantially uniform decrease in diastolic blood pressure using a technique described in greater detail below with reference to FIGS. 2–5. System 8 also includes components for delivering therapy to terminate the episode of apnea and/or prevent additional episodes of apnea from occurring. Additionally, or in the alternative, the pacer/ICD generates warning signals to alert the patient to an episode of apnea, particularly if he or she is sleeping, in an effort to trigger a resumption of normal respiration. Appropriate diagnostic information is also stored in the pacer/ICD for subsequent review by a physician or other medical professional, following transmission of the diagnostic information to a device programmer (not shown in FIG. 1) or other external display device. Apnea detection, therapy delivery and the generation of warning signals are all performed under the control of a pacer/ICD 10 or other cardiac stimulation device.

Insofar as apnea therapy is concerned, system 8 includes a pair of phrenic nerve stimulators 18 and 20 implanted, respectively, near left and right phrenic nerves for delivering diaphragmatic respiratory pacing. Although not shown, additional nerve stimulators may be implanted for use in respiratory pacing, particularly stimulation devices for stimulating the intercostal muscles. Examples of phrenic nerve stimulators are set forth in U.S. Pat. No. 5,056,519 to Vince, entitled "Unilateral Diaphragmatic Pacer" and in U.S. Pat. No. 6,415,183 to Scheiner et al., entitled "Method and Apparatus for Diaphragmatic Pacing". Other respiratory nerves may be stimulated as well. U.S. Pat. No. 5,911,218 to DiMarco, entitled "Method and Apparatus for Electrical Stimulation of the Respiratory Muscles to Achieve Artificial Ventilation in a Patient" describes stimulation of nerves leading to intercostal muscles. The phrenic nerves signals may typically be stimulated at any point along the phrenic nerves. Note, however, that portions of the phrenic nerves pass epicardially over the heart and it may be disadvantageous to mount phrenic nerve stimulators adjacent those portions of the phrenic nerves, as any electrical signals generated by the stimulator near the heart could potentially interfere with proper functioning of the heart.

Diaphragmatic pacing is the preferred method for treating apnea since respiration can be immediately restored to thereby promptly terminate the episode of apnea so as to prevent any extreme deviations in blood chemistry. Diaphragmatic pacing also allows the episode of apnea to be terminated before the patient awakens due to apnea, assuming the patient is currently sleeping. Since most episodes of apnea, including non-obstructive forms of apnea, occur while a patient is asleep, this is a significant advantage. Preventing frequent sleep interruption due to apnea allows the patient have a restful and therapeutic night's sleep, thereby reducing daytime sleepiness and also reducing the risk of daytime accidents caused by the patient accidentally falling asleep, perhaps while driving.

Figure 6:
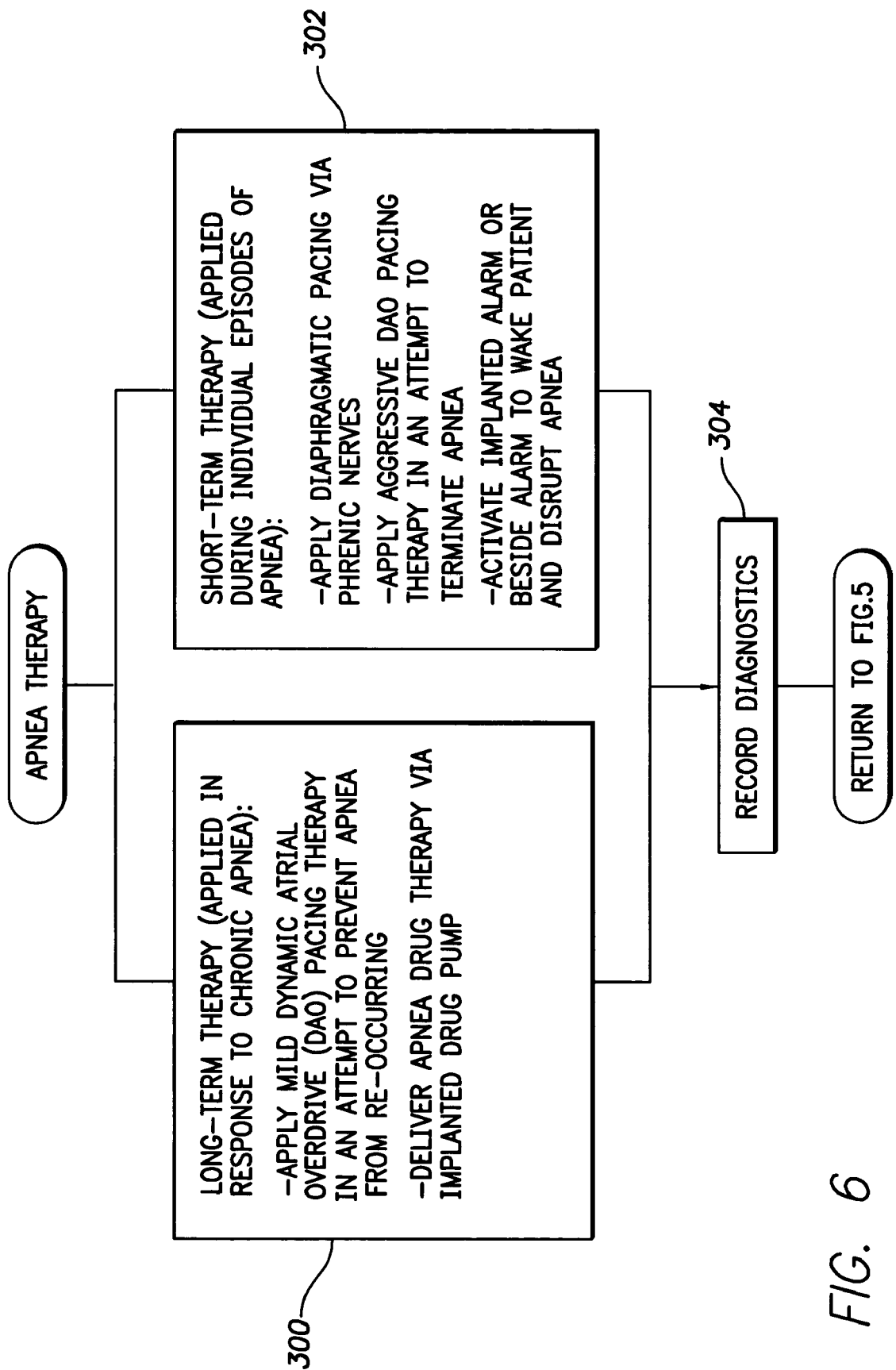
FIG. 6 is a flow diagram illustrating an exemplary therapy to be delivered in response to the detection of an episode of non-obstructive apnea for use with the technique of FIG. 5.

Hence, preferably, phrenic nerve stimulators are employed. If the implanted system is not equipped with nerve stimulators, overdrive cardiac pacing may be employed in an effort to trigger a resumption of respiration so as to terminate the episode of apnea. Overdrive pacing can also help prevent additional episodes of apnea from occurring. Accordingly, overdrive pacing may be advantageously employed in systems that also include phrenic nerve stimulators. Overdrive pacing is delivered using one or more pacing leads implanted in the heart. In FIG. 1, only a single lead is shown. A full set of leads is shown in FIG. 6. Preferably, if diaphragmatic pacing is not available, aggressive overdrive pacing is applied during an episode of apnea in an effort to terminate apnea. Less aggressive overdrive pacing therapy may be applied at other times in an effort to prevent the onset of additional episode of apnea, particularly while the patient is asleep. Techniques for treating sleep apnea using overdrive pacing are set forth in U.S. Patent Application: 2003/0153954 A1 of Park et al., entitled "Sleep Apnea Therapy Device Using Dynamic Overdrive Pacing". A particularly effective overdrive pacing technique, referred to as dynamic atrial overdrive (DAO) pacing, is described in U.S. Pat. No. 6,519,493 to Florio et al., entitled "Methods And Apparatus For Overdrive Pacing Heart Tissue Using An Implantable Cardiac Stimulation Device". The aggressiveness of overdrive pacing may be modulated by adjusting the overdrive pacing rate and related control parameters. See: Published U.S. Patent Application 2003/0130703, of Florio et al., entitled "Method And Apparatus For Dynamically Adjusting Overdrive Pacing Parameters", filed Jan. 9, 2002.

Additionally, or in the alternative, the implantable apnea responsive system may include a drug pump 22 capable of the delivering drug therapy in an attempt to prevent the onset of additional episodes of apnea. Discussions of possible medications for preventing the onset of non-obstructive forms of apnea are provided below. Preferably, upon the detection of initial episodes of sleep apnea, DAO and/or drug therapy is preferably delivered to the patient in an attempt to prevent the onset of additional episodes of apnea. If additional episodes nevertheless occur and the overall system does not include nerve stimulators for directly terminating apnea, then alarm signals are generated to awaken the patient during apnea (if the patient is sleeping) to alert the patient to the episode of apnea so that the patient is awoken, thus triggering a resumption in breathing. As explained above, sleep interruptions are preferably avoided. However, if an episode of apnea cannot be terminated, it is preferable to awaken the patient immediately rather than to allow apnea to continue until the patient is forced to awaken on his or her own. Accordingly, the implanted system includes an internal apnea alarm 24 and/or an external bedside alarm 26. Internal alarm 24 may be a vibrating device or a "tickle" voltage device that, in either case, provides perceptible stimulation to the patient to awaken the patient, thus terminating the episode of apnea. The bedside alarm may provide audible or visual alarm signals of sufficient magnitude to awaken the patient thus also terminating apnea. The bedside alarm is activated by signals sent via wireless transmission methods from the implanted pacer/ICD.

Thus, FIG. 1 provides an overview of an implantable system for detecting non-obstructive forms of apnea and for delivering therapy or warning signals in response thereto. Internal signal transmission lines for interconnecting the various implanted components are not shown. Alternatively, wireless signal transmission may be employed internally. It should be appreciated that the illustrative embodiments described herein need not include all the components shown in FIG. 1. In many implementations, the system will include only the pacer/ICD and its leads. Other implementations will employ phrenic nerve stimulators but no internal or external alarms and no drug pumps. Still other implementations may employ additional components, such as additional nerve stimulators for directly stimulating the intercostal chest muscles associated with respiration. These are just a few exemplary embodiments. No attempt is made herein to describe all possible combinations of components that may be provided in accordance with the general principles of the illustrative embodiments. Note also that the particular locations of the implanted components are merely exemplary.

Overview of Non-Obstructive Apnea Detection Technique

Figure 2:
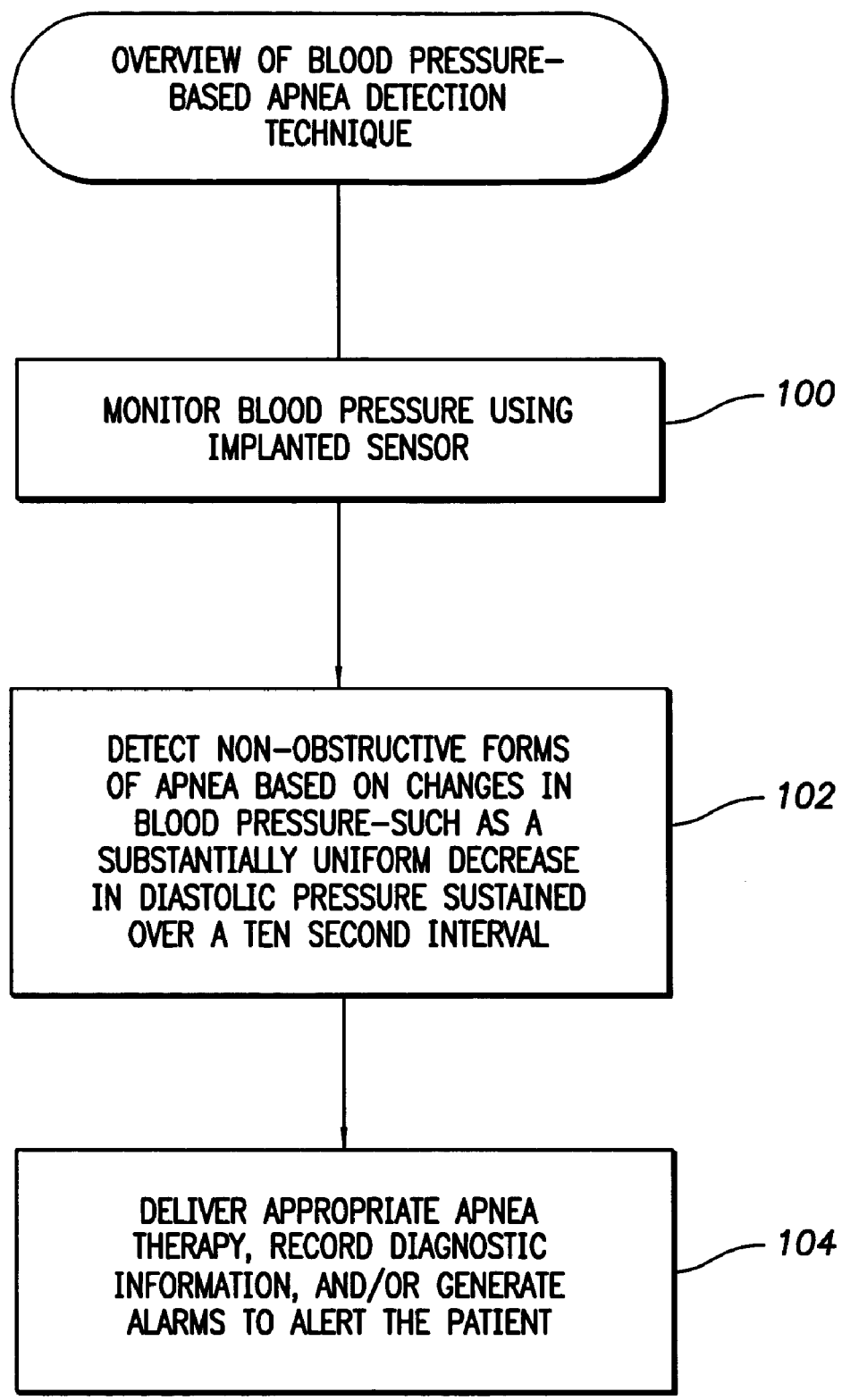
FIG. 2 is a flow diagram providing an overview of the blood pressure-based technique for detecting non-obstructive apnea performed by the system of FIG. 1.

FIG. 2 provides an overview of the apnea detection techniques according to the illustrative embodiments. Initially, at 100, the implantable pacer/ICD monitors blood pressure using an implanted sensor then, at step 102, detects non-obstructive forms of apnea within the patient based on changes in blood pressure. In the preferred embodiment described herein, non-obstructive apnea is detected primarily by identifying a substantially uniform decrease in diastolic blood pressure. If an episode of apnea is detected, then, at step 104, appropriate therapy is delivered, diagnostic information is recorded, and/or alarm signals are generated to alerts the patient to the episode of apnea.

The general technique FIG. 2 is illustrated in the examples of FIGS. 3 and 4. Referring first to FIG. 3, an episode of CSA is illustrated by way of exemplary respiration pattern 106. As can be seen, at about the ten second mark, respiration ceases and an episode of apnea 108 begins. Beat-by-beat diastolic blood pressure is shown via dotted line 110. Each dot represents the diastolic pressure detected for an individual corresponding heartbeat. In an example described below, the diastolic pressure is detected for a given heartbeat at a point midway between the end of a T-wave and the beginning of the next P-wave/A-pulse. As can be seen, prior to apnea, the detected diastolic pressure values are relatively high. Also, so long as respiration is occurring, the detected diastolic pressure values vary over the course of each respiration cycle—generally increasing during inhalation and decreasing during exhalation (subject, in this example, to a bit of time lag.) Hence, during respiration, the rate of change in diastolic pressure from beat to beat varies from positive to negative values. Once the episode of apnea begins, however, the pressure decreases during an interval 112 to a stable baseline pressure 114. The decrease in diastolic pressure is substantially uniform, i.e. the rate of change in diastolic pressure from beat to beat remains near zero during interval 112. Once stable, the diastolic pressure also remains substantially uniform, i.e. the rate of change in diastolic pressure from beat to beat remains near zero during interval 114. Intervals 112 and 114 are detected and timed, using techniques described below with reference FIG. 5, and, if the combined period of time exceeds a predetermined apnea detection time threshold, typically set to ten seconds, apnea is thereby detected. Note that, in some cases, interval 112 will exceed ten seconds in duration and so apnea will be detected even before the blood pressure drops to the stable baseline pressure. In other cases, apnea will not be detected until some time after the pressure reaches the baseline pressure. For example, if interval 112 is only five seconds long, apnea is not detected until five seconds into interval 114. In either case, the total time to detect apnea is the same—ten seconds.

In FIG. 3, a faint line interconnects the dots to emphasize the cyclical change in detected diastolic pressure values occurring while respiration is on-going. During apnea, there is no cyclical change in the detected diastolic pressure values because here is no respiration. (Note that this line does not represent instantaneous blood pressure, which typically changes very significantly over the course of single heartbeat, from systolic phases to diastolic phases. Rather the line represents an interpolation of the individual diastolic pressure values detected for individual heartbeats.)

Turning now to FIG. 4, an episode of apnea arising during CSR is illustrated by way of exemplary respiration pattern 116. CSR is characterized by periodic bursts of respiration (hyperpnea) 118 separated by periods of reduced breathing (hypopnea) 120, which in the example of FIG. 4 is frank apnea. During each burst of respiration, diastolic blood pressure, as represented by dotted line 122, increases significantly until apnea resumes. Again, each dot represents the diastolic pressure detected for an individual corresponding heartbeat. As can be seen, during a respiration burst, the detected diastolic pressure values generally increase, while exhibiting the cyclical variations noted above with reference to FIG. 3. Hence, during the respiration bursts, the rate of change in diastolic pressure from beat to beat varies from positive to negative values. (As in FIG. 3, a faint line interconnects the dots to emphasize the cyclical change in detected diastolic pressure occurring while respiration is occurring.) Once apnea resumes, the detected diastolic pressure values decrease during an interval 124 to a baseline pressure 126. As with the CSA example, the decrease in diastolic pressure at the onset of an episode of apnea is substantially uniform and is followed by a stable baseline interval. The uniform decrease interval and the stable interval are collectively at least ten seconds in duration.

As will be explained in greater detail below, apnea detection based upon the substantially uniform decrease in diastolic pressure may be corroborated using other apnea detection techniques. For example, thoracic impedance signals or accelerometer signals may be additionally analyzed to confirm detection of apnea, with therapy delivered only if the additional signals confirm the onset of apnea. In this manner, the pacer/ICD need not rely upon slower, conventional apnea detection techniques but can nevertheless use those techniques as a secondary tool to help confirm detection. The illustrative embodiment is primarily intended for use in detecting episodes of apnea occurred while a patient is asleep because most episodes of apnea arise during sleep. However, the illustrative embodiment may also be applied to the detection of forms of non-obstructive apnea occurring while patient is awake, as may occur due to CSR triggered by severe CHF. Since blood pressure can vary due to a variety of factors while a patient is awake, corroboration using other apnea detection techniques may be particularly advantageous. While a patient is asleep, corroboration is less important. Note also in FIGS. 3 and 4 that the heart rate, represented by the frequency of the individual dots of lines 110 and 122 is higher while respiration occurs, then decreases once apnea has begun. The decrease in heart rate may also be used to corroborate the detection of apnea.

Thus, FIGS. 3 and 4 illustrate episodes of non-obstructive forms of apnea. Obstructive forms of apnea, e.g. OSA, cannot be detected based upon the uniform decrease in blood pressure. With OSA, blood pressure typically increases significantly because the diaphragm contracts frequently and vigorously in an attempt to achieve adequate ventilation despite upper respiratory airway blockage. Due to the blood pressure differences arising between non-obstructive apnea and obstructive apnea, the blood-pressure-based techniques described herein may also be advantageously used to discriminate between obstructive and non-obstructive forms of apnea (particularly if apnea has already been detected using some other technique.) Additional techniques for discriminating among different types of apnea are discussed in U.S. patent application Ser. No. 10/795,009, to Koh et al., filed Mar. 4, 2004, entitled "System and Method for Distinguishing among Obstructive Sleep Apnea, Central Sleep Apnea and Normal Sleep Using an Implantable Medical System".

Finally, with regard to FIGS. 3 and 4, the respiration and blood pressure patterns shown therein are stylized representations provided merely to illustrate pertinent features of the illustrative embodiments and should not be construed as being representative of actual clinical data. The vertical scale is arbitrary. Features are exaggerated for clarity.

Exemplary Detection Technique with Corroboration

Referring to FIG. 5, a particular exemplary implementation of a non-obstructive apnea detection technique will now be described. This particular example is directed to detecting apnea in circumstances wherein the uniform decrease in blood pressure at the onset of apnea continues for at least ten seconds thereby allowing apnea to be detected based solely on the uniformly decreasing interval. Modifications are discussed below for use in circumstances wherein the blood pressure reaches the stable baseline pressure before ten seconds have elapsed. At step 200, the pacer/ICD sets an apnea detection timer to zero then, at step 202, a current heartbeat (n) is detected. Individual heartbeats may be detected using otherwise conventional techniques, such as by analyzing IEGM signals detected via cardiac pacing leads. At step 204, a value representative of the ventricular diastolic pressure associated with the current heartbeat is detected (using sensor 14 of FIG. 1). The diastolic pressure for heartbeat n is represented herein as BP(n). In general, ventricular pressure may be detected at any time during the diastolic phase so long as the technique is consistent from beat to beat. Preferably, however, the end of the diastolic phase is not used, since ventricular pressure typically increases significantly during the end of the diastolic phase. Elsewhere within the diastolic phase, ventricular pressure is fairly constant. In one example, a point midway between the end of a T-wave and the beginning of the next P-wave/A-pulse is used as a detection period. Next, at step 206, the pacer/ICD determines a value representative of any change in blood pressure by calculating:

$$\Delta BP(n) = BP(n) - BP(n-1).$$

During a first iteration of the steps of FIG. 5, a default value may be used for BP(0). Thereafter, the previous value of the diastolic blood pressure is used as BP(n−1). Next, at step 208, the pacer/ICD determines a value representative of any change in the rate of change of blood pressure by calculating:

$$\Delta\Delta BP = \Delta BP(n) - \Delta BP(n-1).$$

During the first iteration, a default value may be used for $\Delta\Delta BP(0)$. At step 210, the pacer/ICD then seeks to determine whether blood pressure is decreasing by comparing $\Delta BP(n)$ to zero. At step 212, the pacer/ICD then seeks to determine whether the change in the rate of change is substantially uniform. This may be accomplished by comparing $|\Delta\Delta BP(n)|$ to a predetermined rate-based threshold "R". If $|\Delta\Delta BP(n)|$ does not exceed R, the rate of change is deemed to substantially uniform. R may be programmed by the physician. Alternatively, the device may configured to automatically set the value of R based on an examination of values of $|\Delta\Delta BP(n)|$ obtained while the patient is known to be breathing normally. For example, the minimum value for $|\Delta\Delta BP(n)|$ during normal breathing can be ascertained. Then, R is set to some value less than that minimum value. Adaptive techniques may be employed to automatically adjust R to improve apnea detection reliability.

If $\Box BP(n)$ is less than zero and $|\Box\Box BP(n)|$ is less than R (i.e. blood pressure is decreasing and the decrease is substantially uniform), then the apnea detection timer (initially set to zero at step 200) is activated at step 214 (assuming the timer had not already been activated during to a previous iteration of the steps of FIG. 5.) In other words, once the blood pressure is found to be decreasing and that decrease is found to be substantially uniform, the apnea detection timer is activated to begin timing the interval during which the blood pressure continues to decrease at a substantially uniform rate. Thus, the apnea detection timer begins to time intervals such as 112 and 124 of FIGS. 3 and 4. Also at step 214, the pacer/ICD compares the current value of the timer against an apnea detection threshold (T). The apnea detection threshold T may be set, for example, to a value in the range of ten to fifteen seconds. During a first iteration of step 214, the timer will not exceed that threshold and so processing returns to step 202 to allow steps 202–212 to be repeated for the next detected heartbeat. So long as the blood pressure continues to decrease and the decrease remains substantially uniform, step 214 is repeated until the timer value eventually exceeds the threshold T.

At that point, a possible episode of non-obstructive apnea is thereby detected, step 216, and an attempt is made to corroborate the detection. As noted, corroboration may be performed using otherwise conventional apnea detection techniques. In one example, thoracic impedance is detected between one or more leads implanted within the part of the patient and the body of the pacer/ICD. Changes in impedance caused by heartbeats or other non-respiratory factors are filtered out to detect possible respiration. Assuming no respiration occurred during the interval timed by the timer, then apnea is thereby corroborated. However, if respiration did occur during the timed interval, then the detection of possible apnea is rejected, the timer is reset to zero at step 218, and processing resumes at step 202. Thoracic impedance may be detected using any of a variety of otherwise conventional techniques. An example is set forth the U.S. Pat. No. 5,817,135 to Cooper et al. entitled, "Rate-Responsive Pacemaker with Noise-Rejecting Minute Volume Determination". Techniques for detecting apnea based upon respiration are discussed in the patent application to Park et al. cited above.

Corroboration may also be performed based upon a lack of phrenic nerve signals detected via a phrenic nerve sensor, which may be a component of the phrenic nerve stimulators 18 and 20 of FIG. 1. If phrenic nerve signals were detected during the timed interval, then the detection of possible apnea is likewise rejected. If no phrenic nerve signals were detected, apnea is thereby confirmed. Phrenic nerve signals may be detected using any of a variety of otherwise conventional techniques. Examples are set forth in U.S. Pat. No. 3,957,036 to Normann, entitled "Method and Apparatus for Recording Activity in Intact Nerves" and the patent to Scheiner et al. referred to above. Corroboration may also be performed using an accelerometer or other device to detect any motion or activity consistent with respiration. If there is motion or activity consistent with respiration, the episode of apnea is not corroborated. Techniques for detecting motion, activity or activity variance are discussed U.S. Pat. No. 5,476,483, to Bornzin et al., entitled "System and Method for Modulating the Base Rate During Sleep for a Rate-responsive Cardiac Pacemaker". See also: U.S. Pat. No. 6,658,292 to Kroll et al., entitled "Detection of Patient's Position and Activity Status using 3D Accelerometer-Based Position Sensor" and U.S. Pat. No. 6,466,821 to Pianca et al., entitled "AC/DC Multi-Axis Accelerometer for Determining Patient Activity and Body Position." As noted above, changes in heart rate may also be used to corroborate non-obstructive apnea. Leads or motion sensors may also be mounted in the abdomen for detecting motion associated with contraction of the diaphragm and such devices may be used to corroborate apnea.

Thus, a wide variety of techniques are suitable for corroborating detection of an episode of non-obstructive apnea. A few examples have been set forth herein. This does not represent an exhaustive list of possible corroboration techniques. Moreover, the specific form of corroboration may vary depending upon whether the patient is currently asleep or awake. For example, the device may be programmed so as to require two forms of corroboration before therapy is delivered in response to apnea while the patient is a wake; whereas only a single form of corroboration is required if the patient is asleep. Wake/sleep states may be detected using otherwise conventional techniques. A particularly effective technique is set forth in U.S. patent application Ser. No. 10/339,989, to Koh et al., entitled "System and Method for Detecting Circadian States Using an Implantable Medical Device", filed Jan. 10, 2003.

If the episode of apnea is not corroborated, the timer is reset at step 218 and processing resumes at step 202 to allow for eventual detection and monitoring of another interval indicative of possible apnea. In addition, the timer is reset at step 218 if either the blood pressure is not decreasing or the rate of change in blood pressure is not substantially uniform. However, if the episode of apnea is corroborated, then step 220 is instead performed wherein apnea therapy is delivered.

As noted, circumstances can arise wherein the blood pressure reaches the baseline pressure before the timer expires. If so, the interval of uniform decrease will not, by itself, exceed the detection threshold T and the timer should instead track the combined interval, i.e. the interval of uniform decrease in blood pressure plus the subsequent interval of stable baseline pressure. To account for such contingencies, the technique of FIG. 5 may be modified as follows. Instead of immediately resetting the timer at step 218 (due to either $\Box BP(n) \geqq 0$ OR $|\Box\Box BP| \geqq R$), the timer instead remains active to track any immediately subsequent interval wherein $\Box BP(n) \approx 0$ AND $|\Box\Box BP| < R$. If the timer reaches T during the subsequent interval while $\Box BP(n) \approx 0$ AND $|\Box\Box BP| < R$, apnea is thereby detected. In this manner, the combined interval is tracked. Determination of whether $\Box BP(n) \approx 0$ may be performed by comparing the absolute value of $\Box BP(n)$ against a predetermined threshold. If desired, an initial threshold value of, for example, five seconds may be required before tracking of the additional baseline time interval is enabled. In other words, the timer will only be enabled to track the combined interval if there has already been at least several seconds of uniform decrease in pressure. The initial threshold is employed to help avoid false positive detections of apnea. Note that for many patients and for many episodes of apnea occurring within those patients, the technique of FIG. 5 is sufficient to detect the episode and so the modified version is not required. The particular detection technique to be activated within a given pacer/ICD for a particular patient may be a programmable feature set by the physician based, for example, on an examination of the blood pressure changes occurring during apnea within the particular patient.

Exemplary Apnea Therapy and Response Techniques

Apnea therapy is summarized in FIG. 6. Two forms of therapy are provided: long-term therapy and short-term therapy. Long-term therapy is preferably employed at all times within patients who are found to be subject to frequent episodes of non-obstructive apnea, i.e. they suffer from chronic apnea. Short-term therapy is applied only during individual episodes of apnea. Long-term therapy, performed at step 300, includes mild, i.e. "non-aggressive", DAO pacing therapy applied in an attempt to prevent the onset of additional episodes of apnea. Preferably, parameters for controlling DAO therapy are set to values appropriate for reducing the likelihood of additional episodes of apnea. In one example, an overdrive rate set five to ten beats per minute (bpm) above a current intrinsic rate may be employed. Routine experimentation is preferably performed to identify optimal DAO pacing parameters for use with patients subject to non-obstructive apnea to reduce the likelihood of reoccurrence of apnea. The overall aggressiveness of DAO therapy may be adjusted based upon the frequency or duration of the episodes of apnea. DAO references are cited above.

Long-term therapy also includes the delivery of anti-apnea medications via an implantable drug pump, if so equipped. Examples of medications that may be helpful in patients with non-obstructive apnea are set forth the following patents: U.S. Pat. No. 6,331,536 to Radulovacki et al., entitled "Pharmacological Treatment for Sleep Apnea"; U.S. Pat. No. 6,432,956 to Dement et al. entitled "Method for Treatment of Sleep Apneas"; U.S. Pat. No. 6,586,478 to Ackman et al., entitled "Methods and Compositions for Improving Sleep"; and U.S. Pat. No. 6,525,073 to Mendel et al., entitled "Prevention or Treatment of Insomnia with a Neurokinin-1 Receptor Antagonist". Depending upon the particular medication, alternative compounds may be required for use in connection with an implantable drug pump. Routine experimentation may be employed to identify medications for treatment of non-obstructive apnea that are safe and effective for use in connection with an implantable drug pump. Dosages may be titrated based upon the frequency or duration of episodes of apnea.

Short-term therapy, performed at step 302, preferably exploits diaphragmatic pacing, if phrenic nerve stimulators or other suitable nerve stimulators are provided. Diaphragmatic pacing references are cited above. In the alternative, aggressive DAO pacing may be applied during the episode of apnea in an attempt to trigger breathing. In one example, an overdrive rate set ten to twenty bpm above a current intrinsic rate may be employed. Again, routine experimentation is preferably performed to identify optimal DAO pacing parameters for use with patients during an episode of non-obstructive apnea. If diaphragmatic pacing is not available and DAO pacing is not effective for terminating apnea, then alarm or warning signals are preferably generated, if the patient is asleep, to awaken the patient so as to terminate the episode of apnea. As mentioned above, although sleep interruptions are preferably avoided, it is preferable to wake the patient early in the episode of apnea rather than to allow aberrant blood chemistry levels to force the patient to awaken. Whenever some form of therapy is delivered, appropriate diagnostic information is stored at step 304 so that medical professionals can subsequently review the therapy and evaluate its effectiveness.

For the sake of completeness, a description of an exemplary pacer/ICD will now be provided. As many patients who suffer from non-obstructive forms of apnea are also candidates for pacer/ICDs, it is advantageous to configure a pacer/ICD to serve as the controller of the implantable apnea responsive system. The techniques of the illustrative embodiment, however, may be performed using any suitable implantable components.

Exemplary Pacer/ICD

Figure 7:
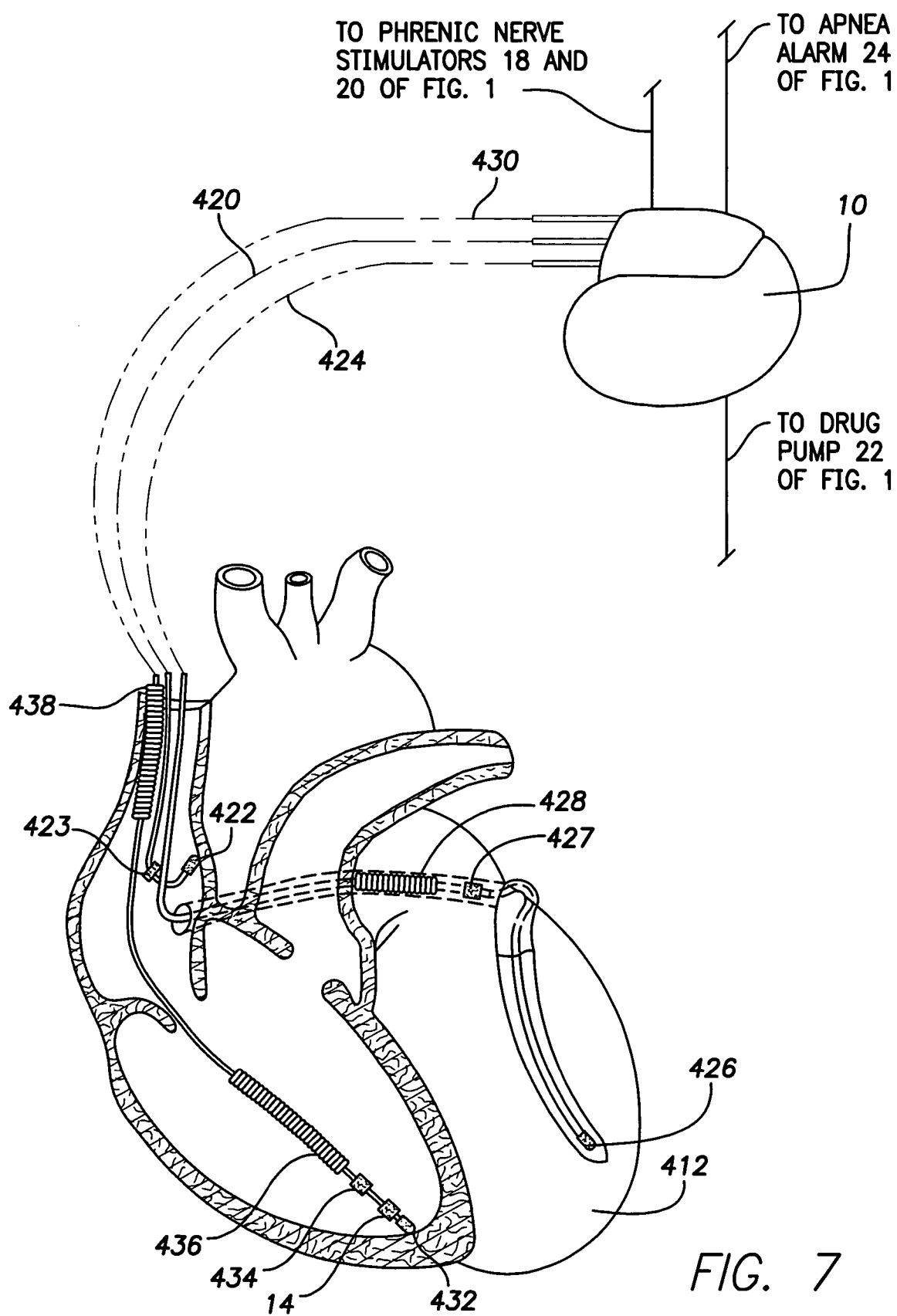
FIG. 7 is a simplified, partly cutaway view, illustrating the pacer/ICD of FIG. 1 along with at complete set of leads implanted into the heart of a patient.
Figure 8:
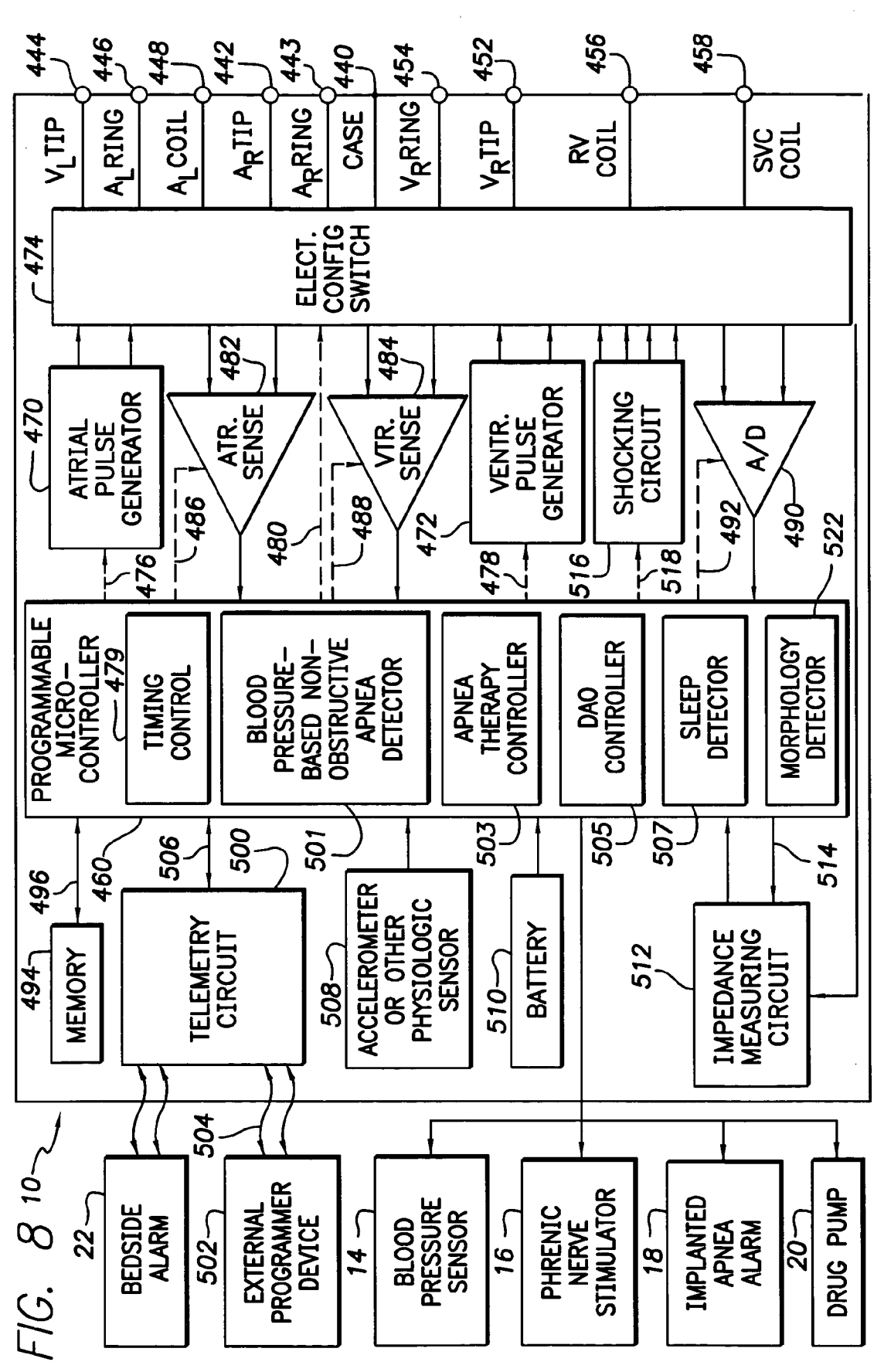

With reference to FIGS. 7 and 8, a description of the pacer/ICD of FIG. 1 will now be provided. FIG. 7 provides a simplified block diagram of the pacer/ICD, which is a dual-chamber stimulation device capable of treating both fast and slow arrhythmias with stimulation therapy, including cardioversion, defibrillation, and pacing stimulation, as well as capable of detecting non-obstructive apnea and controlling delivering of therapy in response thereto.

To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 7, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 8. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 10, shown schematically in FIG. 8, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial tip electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical. Rather, any suitable microcontroller 460 may be used that carries out the functions described herein. The use of microprocessor-based control circuits for performing timing and data analysis functions are well known in the art.

As shown in FIG. 8, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 10 (as contained in the microcontroller 460 or memory 494) to be sent to the external device 502 through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV Delay, V—V Delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 8. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 10 is preferably capable of high voltage therapy and appropriate batteries.

As further shown in FIG. 8, pacer/ICD 10 is shown as having an impedance measuring circuit 512 which is enabled by the microcontroller 460 via a control signal 514. Herein, thoracic impedance is primarily detected for use in tracking thoracic respiratory oscillations for use in confirming apnea. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5–10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Microcontroller 460 also includes various components directed to the detection and treatment of non-obstructive apnea. More specifically, the microcontroller includes a blood pressure-based non-obstructive apnea detection unit 501 operative to detect non-obstructive apnea within the patient based on changes in blood pressure (detected via blood pressure sensor 14) using the techniques described above. An apnea therapy controller 503 operates, also in accordance with techniques described above, to control delivery of apnea therapy and/or the generation of alarm signals. More specifically, the apnea therapy controller operates to control phrenic nerve stimulator 16, implanted apnea alarm 18, drug pump 20, bedside alarm 22 and/or a DAO controller 505. Control may be achieved via wireless communication techniques using telemetry circuit 500 or via direct connections. In FIG. 8, for the sake of clarity, the phrenic nerve stimulator, the implanted apnea alarm, and the drug pump are all shown as being directly connected to the microprocessor. Preferably, however, connection is provided either through the telemetry circuit or through individual connection terminals (not separately shown). Collectively, the apnea therapy controller and any of the individual therapy or alarm devices comprise an apnea treatment system operative in response to detection of non-obstructive apnea to deliver therapy. In some implementations, it may be desirable to detect when the patient is asleep to, for example, select the amount of corroboration required before apnea therapy is delivered. In such implementations, a sleep detector 507 is employed. In many implementations, not all of these components are provided. For example, the pacer/ICD may be provided with either a phrenic nerve stimulator or an implanted alarm but not both. Finally, although several of the internal components are shown as being sub-components of the microcontroller, some or all may be implemented separately from the microcontroller. Depending upon the implementation, the various components of the microcontroller may be separate software modules. The modules may be combined so as to permit a single module to perform multiple functions.

What have been described are various systems and methods for detecting non-obstructive forms of apnea and for delivering therapy in response thereto using an implantable system controlled by a pacer or ICD. However, the illustrative embodiments may be implemented using other implantable systems or in accordance with other techniques. Thus, while the illustrative embodiments have been described, modifications can be made thereto without departing from the spirit and scope of the invention.

What is claimed is:

1. A method for detecting non-obstructive apnea within a patient using an implantable medical system, the method comprising the steps of:
   monitoring diastolic blood pressure; and
   detecting non-obstructive apnea within the patient based on changes in diastolic blood pressure;
   wherein the step of detecting non-obstructive apnea within the patient based on changes in diastolic blood pressure includes the steps of:
   tracking changes in diastolic blood pressure from beat to beat;
   identifying a period of time having a substantially uniform decrease in diastolic blood pressure from beat to beat; and
   associating non-obstructive apnea with the period of time having the substantially uniform decrease in the diastolic blood pressure from beat to beat.

2. The method of claim 1 wherein the period of time is about ten seconds.

3. A method for detecting non-obstructive apnea within a patient using an implantable medical system, the method comprising the steps of:
   monitoring blood pressure; and
   detecting non-obstructive apnea within the patient based on changes in blood pressure;
   wherein the step of detecting non-obstructive apnea within the patient based on changes in blood pressure includes the steps of:
   evaluating BP(n) wherein BP(n) is the blood pressure of a heartbeat "n" for a plurality of beats;
   calculating $\Delta BP(n)=BP(n)-BP(n-1)$ for the plurality of beats;
   calculating $\Delta\Delta BP=\Delta BP(n)-\Delta BP(n-1)$ for the plurality of beats; and
   identifying a period of time wherein $\Delta BP(n)<0$ and $|\Delta\Delta BP|$ is less than a predetermined rate-based threshold value; and
   determining whether the period of time exceeds a predetermined time-based threshold value and, if so, generating a signal indicative of the onset of non-obstructive apnea.

4. The method of claim 3 wherein the step of monitoring blood pressure is performed to monitor diastolic pressure.

5. The method of claim 3 wherein the step of monitoring blood pressure is performed using an implantable pressure sensor.

6. The method of claim 3 wherein the time-based threshold value is in the range of ten to fifteen seconds.

7. The method of claim 3 wherein the time-based threshold value is ten seconds.

8. The method of claim 3 further including the step of delivering apnea therapy in response to the detection of non-obstructive apnea.

9. The method of claim 8 wherein the step of delivering apnea therapy includes the step of delivering overdrive pacing therapy to the heart of the patient.

10. The method of claim 9 wherein the overdrive pacing therapy is dynamic atrial overdrive (DAO) pacing therapy.

11. The method of claim 8 for use with a system having an implantable drug pump and wherein the step of delivering apnea therapy includes the step of selectively delivering drug therapy to the patient using the drug pump.

12. The method of claim 8 for use with a system having an implantable phrenic nerve stimulator and wherein the step of delivering apnea therapy includes the step of delivery of diaphragmatic pacing to the phrenic nerves using the phrenic nerve stimulator.

13. The method of claim 3 further including the step of generating a warning signal in response to non-obstructive apnea sufficient to alert the patient.

14. The method of claim 13 wherein the step of generating a warning signal includes one or more of: transmitting a signal to an external alarm device; electrically stimulating selected muscles of the patient to cause the muscles to twitch using an implantable electrical stimulator; or controlling an implantable vibration device to vibrate.

15. The method of claim 3 further including the step of recording diagnostic information representative of detection of apnea.

16. A method for detecting non-obstructive apnea within a patient using an implantable medical system, the method comprising the steps of:
   monitoring blood pressure;
   detecting non-obstructive apnea within the patient based on changes in blood pressure; and
   detecting patient motion of the type associated with respiration and wherein the step of detecting non-obstructive apnea based on changes in blood pressure is performed only if there is substantially no motion of the type associated with respiration.

17. The method of claim 16 wherein the system includes an accelerometer and wherein the patient motion is detected using the accelerometer.

18. A system for detecting non-obstructive apnea within a patient using implantable medical components, the system comprising:
   a blood pressure detector; and
   a blood pressure-based non-obstructive apnea detector operative to detect non-obstructive apnea within the patient based on changes in diastolic blood pressure;
   wherein the apnea detector tracks changes in diastolic blood pressure from beat to beat, identifies a period of time having a substantially uniform decrease in diastolic blood pressure from beat to beat, and associates non-obstructive apnea with the period of time having a substantially uniform decrease in the diastolic blood pressure from beat to beat.

19. The system of claim 18 wherein the apnea detector detecting non-obstructive apnea within the patient based on changes in diastolic blood pressure further comprises:
   evaluating BP(n) wherein BP(n) is the diastolic blood pressure of a heartbeat "n" for a plurality of beats;
   calculating $\Delta BP(n)=BP(n)-BP(n-1)$ for the plurality of beats;

calculating ΔΔBP=ΔBP(n)−ΔBP(n−1) for the plurality of beats; and identifying a period of time wherein ΔBP(n)<0 and |ΔΔBP| is less than a predetermined rate-based threshold value; and determining whether the period of time exceeds a predetermined time-based threshold value and, if so, generating a signal indicative of the onset of non-obstructive apnea.

20. The system of claim 18 wherein the predetermined period of time is about 10 seconds.

21. The system of claim 18 wherein the substantially uniform decrease in diastolic pressure from beat to beat comprises a rate of change in diastolic pressure from beat to beat to remain near zero.

22. A system for detecting and treating non-obstructive apnea within a patient using implantable medical components, the system comprising:
  a blood pressure-based non-obstructive apnea detector operative to detect non-obstructive apnea within the patient based on changes in diastolic blood pressure; and
  an apnea treatment system operative in response to detection of non-obstructive apnea to deliver therapy;
  wherein the apnea detector tracks changes in diastolic blood pressure from beat to beat, identifies a period of time having a substantially uniform decrease in diastolic blood pressure from beat to beat, and associates non-obstructive apnea with the period of time having a substantially uniform decrease in the diastolic blood pressure from beat to beat.

23. The system of claim 22 wherein the apnea treatment system includes a diaphragmatic pacing system operative to deliver diaphragmatic pacing.

24. The system of claim 22 wherein the apnea treatment system includes an overdrive pacing system operative to deliver overdrive pacing to the heart of the patient.

25. The system of claim 22 wherein the apnea detector detecting non-obstructive apnea within the patient based on changes in diastolic blood pressure further comprises:
  evaluating BP(n) wherein BP(n) is the diastolic blood pressure of a heartbeat "n" for a plurality of beats;
  calculating ΔBP(n)=BP(n)−BP(n−1) for the plurality of beats;
  calculating ΔΔBP=ΔBP(n)−ΔBP(n−1) for the plurality of beats; and
  identifying a period of time wherein ΔBP(n)<0 and |ΔΔBP| is less than a predetermined rate-based threshold value; and
  determining whether the period of time exceeds a predetermined time-based threshold value and, if so, generating a signal indicative of the onset of non-obstructive apnea.

26. The system of claim 22 wherein the predetermined period of time is about 10 seconds.

27. The system of claim 22 wherein the substantially uniform decrease in diastolic pressure from beat to beat comprises a rate of change in diastolic pressure from beat to beat to remain near zero.

28. A system for detecting non-obstructive apnea within a patient using implantable medical components, the system comprising:
  means for detecting diastolic blood pressure;
  means for tracking changes in diastolic blood pressure;
  means for identifying a period of time having a substantially uniform decrease in diastolic blood pressure; and
  means for associating non-obstructive apnea with the period of time having the substantially uniform decrease in the diastolic blood pressure.

29. The system of claim 28 wherein the means for associating non-obstructive apnea with the period of time having the substantially uniform decrease in the diastolic blood pressure further comprises:
  evaluating BP(n) wherein BP(n) is the diastolic blood pressure of a heartbeat "n" for a plurality of beats;
  calculating ΔBP(n)=BP(n)−BP(n−1) for the plurality of beats;
  calculating ΔΔBP=ΔBP(n)−ΔBP(n−1) for the plurality of beats; and
  identifying a period of time wherein ΔBP(n)<0 and |ΔΔBP| is less than a predetermined rate-based threshold value; and
  determining whether the period of time exceeds a predetermined time-based threshold value and, if so, generating a signal indicative of the onset of non-obstructive apnea.

30. The system of claim 28 wherein the predetermined period of time is about 10 seconds.

31. The system of claim 28 wherein the substantially uniform decrease in diastolic pressure from beat to beat comprises a rate of change in diastolic pressure from beat to beat to remain near zero.

* * * * *